United States Patent [19]

McCarthy et al.

[11] 4,217,798
[45] Aug. 19, 1980

[54] AUTOMATED TEST TUBE STOPPER REMOVER

[75] Inventors: Charles J. McCarthy, Rockville; Maurice Green, Silver Spring, both of Md.

[73] Assignee: The United States of America as represented by the Department of Health, Education and Welfare, Washington, D.C.

[21] Appl. No.: 34,560

[22] Filed: Apr. 30, 1979

[51] Int. Cl.³ .............................................. B67B 7/08
[52] U.S. Cl. ..................................... 81/3.2; 53/381 A
[58] Field of Search .......................... 53/381 R, 381 A; 81/3.1 R, 3.2, 3.31

[56] References Cited

U.S. PATENT DOCUMENTS

| | | | |
|---|---|---|---|
| 2,612,065 | 9/1952 | Packer et al. | 81/3.2 |
| 2,634,036 | 4/1953 | Griswold | 81/3.2 X |
| 2,709,936 | 6/1955 | Brennan | 81/3.2 |
| 2,747,443 | 5/1956 | Vandre | 81/3.2 |
| 2,913,937 | 11/1959 | Benson | 81/3.2 |
| 3,845,605 | 11/1974 | Hartness | 53/381 A X |

*Primary Examiner*—James G. Smith
*Attorney, Agent, or Firm*—Browdy and Neimark

[57] ABSTRACT

A device for removing the stopper from the top of a test tube without exposing the user to hazardous aerosols. The stoppered test tube is inserted upwardly through a vertical passage leading to a chamber. A horizontal air cylinder has a piston rod extending into the chamber, with a pivoted stopper-removing plunger member extending over the passage and having a tail portion which is sealingly engageable with a normally vented sensor nozzle responsive to contact of the top of the stoppered test tube with the plunger member. Closure of the sensor nozzle activates a fluidic back pressure switch, which in turn actuates a fluidic control circuit having two slide valves which respectively operates the air cylinder and simultaneously connects a vacuum source to the chamber. A horizontal slide sensor in the vertical passage is extended to engage the test tube and prevents retraction of the plunger member. Upon withdrawal of the unstoppered test tube, the slide sensor is released and is further extended, causing resetting of the fluidic control circuit to its normal condition, retraction of the plunger member, venting of the sensor nozzle, and retraction of the slide sensor.

14 Claims, 2 Drawing Figures

AUTOMATED TEST TUBE STOPPER REMOVER

FIELD OF THE INVENTION

This invention relates to automatic closure-removing devices for receptacles, and more particularly to an apparatus for removing the stoppers from the tops of test tubes in a way to reduce the hazards from dangerous aerosols created when the stoppers are removed.

BACKGROUND OF THE INVENTION

In recently developed types of clinical laboratory operations involving the use of partially evacuated test tubes, a safety need has arisen because of a hazard which occurs during the act of removing the rubber stopper from such a test tube, such as a test tube of the "Vacutainer" type. The possibility exists that aerosols created, such as by the sudden rush of air into partially evacuated tubes or by the mechanical flexure of the rubber stopper as it separates from the tube, may bring our hazardous materials to be breathed by personnel in the area.

There do not appear to be any previously available devices capable of circumventing this hazard.

A preliminary search of the prior art reveals the following prior U.S. Pat. Nos. of interest:
  Packer et al,—2,612,065
  Griswold,—2,634,036
  Brennan,—2,709,936
  Vandre,—2,747,443
  Benson,—2,913,937

Also, Becton-Dickinson of Rutherford, N.J. 07070 has made a Vacutainer Stopper Remover, Part #4999.

SUMMARY OF THE INVENTION

An object of the invention is to provide for safe removal of container covers, particularly of stoppers from tubes containing potentially dangerous materials.

Another object of the present invention is to provide a device for safely removing the stopper from the top of a test tube which overcomes the deficiencies and disadvantages of previously available stopper-removing devices.

A further object of the invention is to provide a novel and improved test tube stopper-removing device which is free of hazards caused by aerosols created by the removal of a stopper from a test tube.

A still further object of the invention is to provide an improved fluid pressure-operated stopper-removing device for safely removing stoppers from test tubes, particularly from test tubes of the partially evacuated type, the device being simple in construction, reliable in operation, and, preferably embodying fluidic or electrical components.

A still further object of the invention is to provide an improved stopper-removing device for test tubes which may exclusively employ fluidic components and control circuits, with no requirements for the use of electrical energy with its inherent hazards, and which is relatively compact in size, durable in construction, and simple to operate.

A still further object of the invention is to provide an improved device for safely removing stoppers from test tubes, the device employing relatively inexpensive components, such as an inexpensive air cylinder and easily available other fluidic components, and relying on fluidic back pressure sensing, which is in itself a very simple and reliable technique.

In a device according to the present invention the top of the test tube is placed in a chamber before the stopper is automatically removed. Any aerosols created by the removal of the stopper are immediately drawn out through a biological filter. Thus, the operator holds a tube by the bottom while pushing the stoppered end up through a receiving passage. As soon as the stopper reaches a proper height inside the chamber, a vacuum valve opens, pulling a rush of air up through the same passage in the annular space around the tube. At the same time, a plunger member drives forward, knocking the stopper off and allowing it to fall into a collection receptacle. The tube is then withdrawn, the plunger member is reversed, and the vacuum is cut off. In practice, the operator need not pause or release the tube. He simply inserts it upwardly until he feels an inhibition of further upward movement, after which he withdraws the tube downwardly without its stopper.

The device includes an air cylinder driving a toothed plunger member against the side of the stopper, rolling it off in the same manner as an operator holding the tube with his fingers and using his thumb to roll off the stopper. Above and forward of the toothed-edge plunger portion is a plunger extension or stop bar element which is engaged by the top of the stopper. This stop bar, in addition to controlling the height to which the stoppered tube is inserted, also acts to trigger a fluidic back pressure switch. The fluidic back pressure switch imputs to a fluidic flip-flop which supplies pilot pressure to a pair of fluid pressure-operated slide valves. One slide valve sends working pressure to the air cylinder for driving off the stopper, while the other slide valve opens the stopper chamber to a vacuum source. In addition, pressure is supplied to a slide sensor for detecting tube presence and preventing plunger return until the tube is withdrawn.

The slide sensor has three positions. Before a tube is inserted, the slide is pulled back by a vacuum applied at the back end of its housing. Next, when the tube is inserted, the vacuum is changed to a pressure and the slide moves forward to touch the side of the tube. When the tube is removed, however, the sensor slide is driven forward an additional distance until a port is uncovered. This port admits pressure to the flip-flop's complementary input, causing the slide valves to return to their original positions and the sensor slide to be drawn back into its housing.

BRIEF DESCRIPTION OF THE DRAWINGS

Further objects and advantages of the invention will become apparent from the following description and claims, and from the accompanying drawings, wherein:

DESCRIPTION OF A PREFERRED EMBODIMENT

Figure 1:
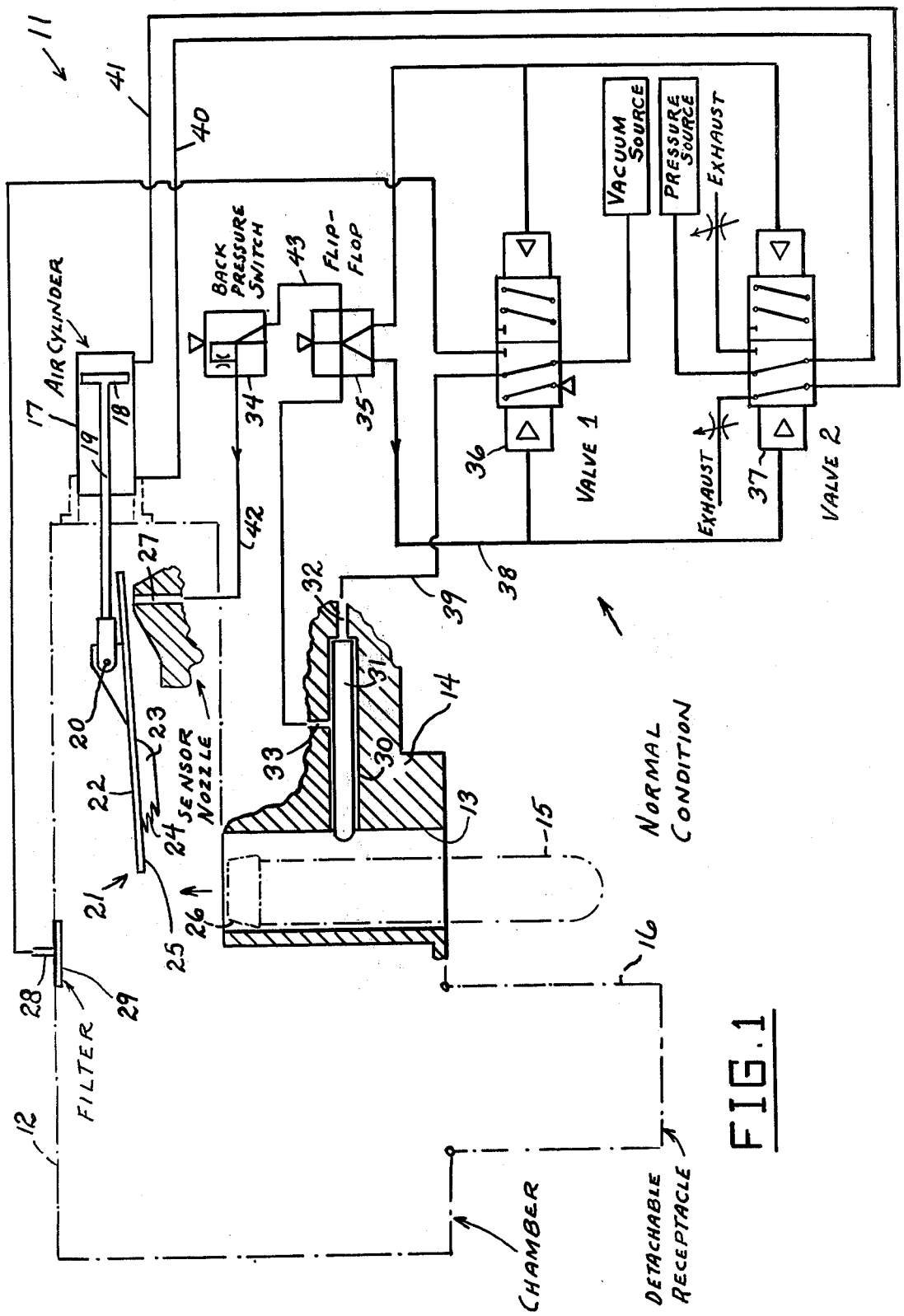
FIG. 1 is a generally schematic diagram of an improved test tube stopper-removing device according to the present invention, shown in normal condition ready to receive a test tube whose stopper is to be removed.

Referring to the drawings, a typical test tube stopper removing device according to the present invention is designated generally at 11. The device 11 comprises a stationary chamber 12 formed with a vertical passage 13 in a bottom duct portion 14 accessible from below for the insertion manually of a stoppered test tube 15. The housing 12 is provided laterally adjacent to the insertion passage 13 with a depending detachable stopper-collecting receptacle 16, such as a clear pastic bag, or the like.

Figure 2:
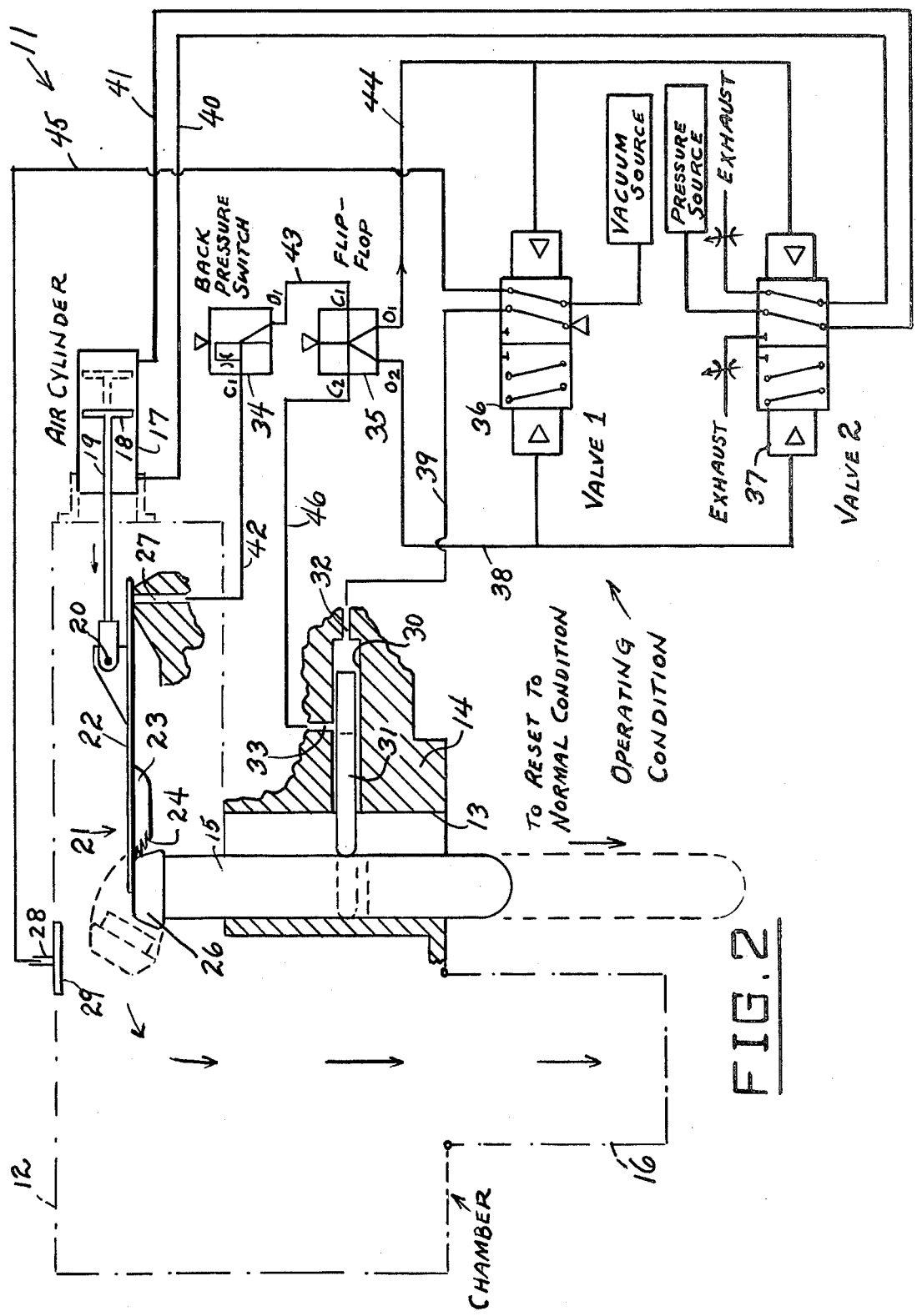
FIG. 2 is a schematic diagram similar to FIG. 1 but showing the stopper-removing device in an operating condition, with a test tube inserted and whose stopper is being removed.

Rigidly secured to the right end wall of chamber 12, as viewed in FIG. 1, is a horizontal air cylinder 17 having a piston 18 and a piston rod 19, which extends into chamber 12. Pivotally connected at 20 to the end of piston rod 19 is a plunger member 21 comprising an elongated flat main plate-like member 22 provided at its left end portion with a depending lug 23 having stopper-gripping serrations or teeth at its left end edge. The lug 23 is spaced from the left end of plate-like member 22 to define an extension arm 25 which normally overlies the top of passage 13 so as to be engageable by the rubber stopper 26 of a test tube 15 as it is elevated in passage 13, as shown in FIG. 2. When the test tube is in this elevated position, leftward driving extension of piston rod 19 by air cylinder 17 causes the lug teeth 24 to grippingly engage rubber stopper 26 and roll the stopper off the top of the test tube, as shown in dotted view in FIG. 2, and to allow the disengaged stopper to drop into the collection receptacle 16.

The right end portion of the chamber 12 is provided below the right end portion of plate-like member 22 with an upwardly opening nozzle element 27 which is normally exposed to atmosphere, as shown in FIG. 1, but which is sealed by member 22 when said member 22 is rotated clockwise, as viewed in FIG. 1, by the stopper 26 when the test tube 15 is elevated to the position of FIG. 2.

The chamber 12 is provided with a vacuum port 28 located in a wall portion thereof adjacent to the region above the insertion passage 13, namely, in a position to induce an inward flow of air from the atmosphere upwardly through the space around the test tube 15 in passage 13 when the stopper 26 is removed, as will be presently explained, to prevent outward back flow of hazardous aerosols from the top of the test tube when the stopper is removed. A suitable biological filter 29 is provided in chamber 12, secured around and covering the intake end of port 28.

The duct portion 14 adjacent passage 13 is formed with a horizontal bore 30 containing a slidably-mounted sensor plunger 31. Normally, plunger 31 is in the retracted position of FIG. 1 by vacuum applied to a port 32 at the inner end of bore 30. The plunger 31 may be extended to engage test tube 15, as will be presently described, in the position of the test tube shown in FIG. 2, by the application of positive air pressure to port 32. A reset passage 33 is provided in wall portion 14, opening to the intermediate portion of bore 30, and being located so that said positive pressure may be delivered to said passage 33 when the plunger 31 is extended to the dotted view position of FIG. 2, namely, to a position engaging the opposite wall surface of passage 13, when the unstoppered test tube 15 is lowered to its dotted view position of FIG. 2. As will be presently explained, this resets the device 11 to its normal condition.

The device 11 is provided with a fluidic control circuit comprising a fluidic back pressure switch 34, similar to the Corning Back Pressure Switch, Part No. 191479, a fluidic flip-flop switch 35, similar to Corning Flip-Flop Switch, Part No. 191446, and fluidic slide valves 36 and 37, similar to Corning Slide Valve, Part No. 191594. These components are available from Corning Glass Works, Corning, N.Y. In the diagrams of FIGS. 1 and 2, the delta symbol (∇) denotes a source of positive air pressure. In the normal condition shown in FIG. 1, with nozzle 27 open, the flip-flop 35 is in a state applying positive pressure to a fluid line 38 and therefore placing slide valves 36 and 37 in a condition as shown in FIG. 1. In this condition, vacuum is applied to port 32 via a line 39 and valve 36, positive air pressure is applied to the left end portion of air cylinder 17 via a line 40 and valve 37, and the right end portion of cylinder 17 is exhausted via a line 41 and valve 37. Thus, piston rod 19 and sensor plunger 31 are held in the retracted positions of FIG. 1.

When a stoppered test tube 15 is inserted in passage 13 and is elevated to the position of FIG. 2, member 22 is rotated clockwise and seals port 27. Port 27 is connected to the sensing port of back pressure switch 34 by a line 42. Through this line 42 pressure builds up and actuates switch 34, delivering positive pressure to the right side sensing port of flip-flop 35 via a line 43. This transfers positive pressure via a line 44 to the right ends of valves 36 and 37, reversing said valves and placing them in the conditions of FIG. 2. In this state, positive air pressure is applied to the right end portion of air cylinder 17 via line 41, and the left end portion of cylinder 17 is allowed to exhaust via line 40. Piston rod 19 is extended leftwardly, causing serrated lug 23 to roll off the stopper 26, as shown in dotted view. At the same time, port 28 is connected to vacuum via a line 45 and valve 36, causing the above-mentioned rush of air upwardly through passage 13 past the test tube 15, whereby to prevent the escape of hazardous aerosols. Positive pressure applied to port 32 via line 39 and valve 36 causes sensor plunger 31 to engage test tube 15, as shown in full-line view in FIG. 2.

The intermediate passage 33 is connected to the left-side operating port of flip-flop 35 by a line 46. When the unstoppered test tube 15 is manually moved downwardly in passage 13 to the dotted view position thereof shown in FIG. 2, the pressurized plunger 31 moves to its dotted view position, engaging the opposite wall of passage 13, uncovering port 33. This connects positive pressure to the left-side sensor port of flip-flop 35 and causes said flip-flop to return to its normal state of FIG. 1.

The leftward movement of member 22 vents the nozzle 27, deactivating the switch 34 and releasing pressure in the line 43. Flip-Flop 35 does not change state with the release of pressure at its input or sensor port but only with the application of pressure to the one port that would cause a change of state. This is why pressure must be released at one input before it is applied at the other. And in the interim, with no pressure at either input, the flip-flop remains stable in its previous state. The member 22 need only close nozzle 27 long enough to cause a change of state in flip-flop 35. After that the member 22 moves leftward with its right end sliding off of the nozzle 27 which allows the member 22 to rotate further in the clockwise direction as the rolling stopper 26 pushes the left end of the member 22 upward.

Thus, positive pressure is again applied to fluid line 38, restoring slide valves 36 and 37 to their normal conditions, and piston rod 19 and sensor plunger 31 are retracted to the positions of FIG. 1.

In operation, when a stoppered test tube, such as a blood collection tube is inserted to its upper limit in passage 13, the member 22, which may comprise an elongated aluminum plate, is caused to block air flow from the sensor nozzle 27 so that air is no longer escaping from the control port of the back pressure switch 34. This operates flip-flop 35 to the state of FIG. 2, causing the stopper 26 to be removed and vacuum to be applied to the interior of the chamber 12. This induces an upward rush of air through passage 13, preventing the escape of hazardous aerosols as the test tube becomes unstoppered. When the opened test tube is removed from the passage 13, the device is automatically returned to the state of FIG. 1, with nozzle 27 open and plungers 23 and 31 retracted.

While a specific embodiment of an improved test tube stopper-removing apparatus has been disclosed in the foregoing description, it will be understood that various modifications within the scope of the invention may occur to those skilled in the art. Therefore it is intended that adaptations and modifications should and are intended to be comprehended within the meaning and range of equivalents of the disclosed embodiment.

What is claimed is:

1. A test tube stopper-removing device comprising a chamber, duct means provided on said chamber and defining a passage for inserting a stoppered test tube into the chamber from below so that the test tube can be moved vertically to elevate its stopper into the chamber, positive fluid pressure source means, a vacuum source, a fluid pressure cylinder secured to the chamber and having piston rod means movable in the chamber, a stopper-removing plunger member pivotally connected to said piston rod means, said plunger member being located so as to be engageable by the stopper of a test tube as the test tube is elevated in said passage, means to operatively connect said positive fluid pressure source means to said cylinder to extend said piston rod means and to drive said plunger member laterally against a stopper responsive to engagement of the upwardly moving stopper with the plunger member, so as to remove the stopper from its test tube, and means to communicatively connect said chamber to said vacuum source simultaneously with the removal of the stopper, whereby to induce a rush of air upwardly through said passage and prevent the escape of aerosols from the unstoppered test tube.

2. The stopper-removing device of claim 1, and test tube sensing means in said passage.

3. The stopper-removing device of claim 2, and wherein said sensing means comprises a sensing element movable into engagement with a test tube in the passage when the positive pressure source means is operatively communicatively connected to the cylinder.

4. The stopper-removing device of claim 3, and means to maintain said sensing element retracted prior to the insertion of a test tube into the passage.

5. The stopper-removing device of claim 3, and wherein said duct means is provided with a substantially horizontal bore slidably containing said sensing element, and means normally communicatively connecting the inner end of the bore to said vacuum source.

6. The stopper-removing device of claim 5, and means communicatively connecting the inner end of said bore to said positive pressure source means in place of said vacuum source when said fluid pressure cylinder is activated to extend said piston rod means.

7. The stopper-removing device of claim 6, and means to reverse the fluid pressure cylinder to retract the plunger member while said positive pressure source means is communicatively connected to said bore, responsive to the subsequent withdrawal of the test tube from the passage.

8. The stopper-removing device of claim 1, and wherein the means to operatively connect the positive fluid pressure source means to the cylinder comprises back pressure-responsive valve means connected between said cylinder and said positive pressure source means, and means to develop back pressure in said valve means responsive to the engagement of an upwardly moving test tube stopper with said pivotally connected plunger member.

9. The stopper-removing device of claim 8, and wherein said means to develop back pressure comprises normally vented nozzle means in the chamber adjacent to said pivotally connected plunger member and being sealingly engageable by the pivotally connected plunger member when the plunger member is engaged by an upwardly moving test tube stopper, means communicatively connecting said nozzle means to said positive pressure source means, normally closed control valve means connected between the positive pressure source means and the cylinder, and means to open said control valve means responsive to back pressure developed in said nozzle means.

10. The stopper-removing device of claim 9, and sensing means in said passage, sensing the presence of a test tube therein while the test tube is being unstoppered and maintaining said plunger member extended until the unstoppered test tube is removed from the passage.

11. The stopper-removing device of claim 10, and wherein said duct means has a bore transversely intersecting said passage and said sensing means comprises a sensing plunger slidably mounted in said bore, means normally communicatively connecting the inner end of said bore to said vacuum source, and means substituting said positive pressure source means for said vacuum source responsive to the back pressure developed in said nozzle means.

12. The stopper-removing device of claim 11, and means to maintain said positive pressure source means operatively connected to said cylinder to maintain the piston rod means extended as long as said sensing plunger engages a test tube in said passage.

13. The stopper-removing device of claim 12, and means to reverse said control valve means and retractively connect said positive pressure source means to said cylinder when said sensing plunger no longer engages a test tube in said passage.

14. The stopper-removing device of claim 13, and means to communicatively reconnect the inner end of said bore to said vacuum source in place of said positive pressure source means when said sensing plunger no longer engages a test tube in said passage.

* * * * *